United States Patent
Garapati et al.

(10) Patent No.: US 11,773,039 B2
(45) Date of Patent: Oct. 3, 2023

(54) INTEGRATED PROCESS AND CU/ZN-BASED CATALYST FOR SYNTHESIZING METHANOL UTILIZING CO2, GENERATING ELECTRICITY FROM HYDROCARBON FEEDSTOCK

(71) Applicant: Indian Oil Corporation Limited, Mumbai (IN)

(72) Inventors: Siva Rama Krishna Garapati, Faridabad (IN); Meeta Sharma, Faridabad (IN); Mani Ramya, Faridabad (IN); Rajesh Muralidhar Badhe, Faridabad (IN); Alok Sharma, Faridabad (IN); Gurpreet Kapur Singh, Faridabad (IN); Sankara Sri Venkata Ramakumar, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 0 days.

(21) Appl. No.: 17/937,099

(22) Filed: Sep. 30, 2022

(65) Prior Publication Data

US 2023/0104011 A1    Apr. 6, 2023

(30) Foreign Application Priority Data

Oct. 1, 2021    (IN) .............................. 202121044692

(51) Int. Cl.
     *C07C 29/151*    (2006.01)
     *C01B 3/16*    (2006.01)
     *C07C 29/154*    (2006.01)

(52) U.S. Cl.
     CPC ............ *C07C 29/1518* (2013.01); *C01B 3/16* (2013.01); *C07C 29/154* (2013.01); *C01B 2203/061* (2013.01); *C01B 2203/1076* (2013.01)

(58) Field of Classification Search
     CPC ..... C07C 29/1518; C07C 29/154; C01B 3/16; C01B 2203/061; C01B 2203/1076
     See application file for complete search history.

(56) References Cited

U.S. PATENT DOCUMENTS

| 3,923,694 A | 12/1975 | Cornthwaite |
| 7,384,985 B2 | 6/2008 | Lattner |

(Continued)

FOREIGN PATENT DOCUMENTS

| CN | 102000578 A | 4/2011 |
| EP | 1277699 B1 | 4/2005 |

(Continued)

OTHER PUBLICATIONS

Fan, Ronggang et al., "Preparation and application of Cu/ZnO catalyst by urea hydrolysis method for low-temperature methanol synthesis from syngas", Fuel Processing Technology, Jun. 23, 2017, pp. 69-77, 167.

*Primary Examiner* — Jafar F Parsa
(74) *Attorney, Agent, or Firm* — Workman Nydegger

(57) ABSTRACT

The present disclosure provides an integrated process and a Cu/Zn-based catalyst system for synthesizing methanol from $CO_2$ and generating electricity from hydrocarbon feedstock. The process includes steps of gasifying hydrocarbon feedstock into syngas by using oxygen and using the produced syngas as a fuel in a power generation unit, reusing a first part of an exhaust stream of the power generation unit as a reactant in the gasification unit. Using a second part of the said exhaust stream as a reactant for methanol synthesis in a methanol reactor, wherein, the second part is treated to separate $CO_2$ and water, and $CO_2$ is used as the reactant for methanol synthesis. Operating an electrolyzer during non-peak hours to produce hydrogen, wherein, a required stoichiometric ratio of the produced hydrogen is transferred into the methanol reactor for methanol synthesis, wherein, a (Continued)

Cu/Zn-based catalyst system is used for methanol synthesis through a direct hydrogenation reaction of $CO_2$.

9 Claims, 5 Drawing Sheets

(56) References Cited

U.S. PATENT DOCUMENTS

| | | |
|---|---|---|
| 7,820,128 B2 | 10/2010 | Polier et al. |
| 2006/0235090 A1 | 10/2006 | Nielsen et al. |

FOREIGN PATENT DOCUMENTS

| | | |
|---|---|---|
| EP | 1871731 B1 | 12/2012 |
| EP | 2914904 B1 | 10/2019 |
| GB | 2574117 B | 5/2020 |
| WO | 2010102971 A1 | 9/2010 |
| WO | 2014096249 A1 | 6/2014 |
| WO | 2020044286 A1 | 3/2020 |
| WO | 2020154075 A1 | 7/2020 |

…

INTEGRATED PROCESS AND CU/ZN-BASED CATALYST FOR SYNTHESIZING METHANOL UTILIZING CO2, GENERATING ELECTRICITY FROM HYDROCARBON FEEDSTOCK

FIELD OF THE INVENTION

The present invention relates to an integrated process and a catalyst system that combines waste management, power generation, reduction of CO2 footprints, fuel generation and CO2 utilization. Specifically, the present invention relates to an integrated process and catalyst system for producing syngas from hydrocarbon feedstock, utilizing the produced syngas inside a power generation unit for electrical power generation, and using the carbon dioxide from the said power generation unit as a reactant for methanol synthesis.

BACKGROUND OF THE INVENTION

Generally, the hydrocarbon feedstock like biomass waste, coal, petcoke etc. are converted into syngas which is utilized in the form of liquid fuels or directly used for electricity power generation. However, this process produces waste byproducts while converting the hydrocarbon feedstock into syngas and produces carbon dioxide as a byproduct from the burning of syngas during electricity power generation. Some of the prior art documents are discussed herein below which discloses the use of hydrocarbon feedstock for production of syngas and use thereof in different applications.

EP2914904A2 provides a method for using biomass waste to power and heat generation. The process includes biomass gasification and pyrolysis to produce syngas. The CO2 from the syngas is separated and sent to power generation. The CO2 produced in the power generation step is also captured and combined with the CO2 separated from the syngas. The CO2 is used as a plasma gas, a nutrient for the cultivation of algae and distributed as marketable products.

GB2574117B provides a methanol synthesis method from syngas that is obtained from steam reforming/autothermal reforming of natural gas or gasification of biomass/coal. The process also explains a method for stripping the unreacted gases from the crude methanol and utilizing it further for methanol synthesis.

WO2020044286 explains a method for producing methanol from syngas that is preferably obtained from partial oxidation/autothermal reforming/steam reforming of hydrocarbons or gasification of carbon sources like coal, biomass and municipal solid waste. The process also consists of a hydrogen recovery unit for producing enriched hydrogen stream along with a water gas shift reactor. The enriched gases are again used in the methanol synthesis loop.

WO2020154075 provides a method for producing methanol from hydrocarbons catalytic partial oxidation. The gases from CPO reactor are sent to the methanol reactor post which the product mixture is separated into crude methanol, purge gas (CO and H2), CO2 and hydrogen streams. The CO2, purge gas and hydrogen streams are recycled further to get better conversion.

EP1871731B1 directs a method for capturing CO2 from power plants/industrial plants/atmosphere by using a suitable adsorbent and then reducing the captured CO2 to form formaldehyde-formic acid mixture which is further reacted under suitable conditions to form methanol.

WO2014096249A1 gives an integrated method for producing methanol from syngas and dimethyl ether. The syngas is obtained from steam reforming or partial oxidation reactions and is reacted with DME under suitable reaction conditions to form methanol and methyl acetate.

US20060235090A1 claims a process for the production of methanol from H2, CO and CO2. The method includes conversion of the feed gases to a methanol-aldehyde-ketone mixture and cooling the same followed by hydrogenation of the cooled mixture to form a methanol rich product stream.

U.S. Pat. No. 7,384,985B2 claims a process for producing methanol from synthesis gas. The process involves passing the syngas through a series of catalyst beds in counter current to a liquid layer that flows across the beds. The liquid layer provides the dual purpose of extracting the methanol from the flowing gas thereby pushing the forward reaction as well as gas cooling.

EP1277699B 1 discloses a process for producing syngas by steam reforming of hydrocarbons and then recovering the CO2 from the product gas by a CO2 recovery apparatus. The CO2 is recycled back into the reformer for further synthesis of syngas. The produced syngas is utilised for methanol synthesis in a reactor.

WO2010102971A1 explains a process for producing methanol from syngas obtained through reforming of hydrocarbons. The syngas is reacted to form crude methanol from which CO2 is recovered and recycled back to the reforming process. The crude methanol is further processed to obtain a high purity methanol.

CN102000578A claims a catalyst composed of CuO, ZnO, Al2O3 and MgO at a weight ratio of A:B:C:D, wherein A:B=1/5-5/1, C=1-10% for catalytic hydrogenation of CO2 for producing methanol. The catalyst is prepared by co-precipitation method using oxalic acid-ethanol solution or oxalic acid-water solution. In comparison to the Cu—ZnO-Al2O3 catalyst, claimed catalyst has better activity, stability and methanol selectivity.

Ronggang Fan et al. titled "preparation and application of Cu/ZnO catalyst by urea hydrolysis method for low-temperature methanol synthesis from syngas" Fuel Processing Technology, Vol. 167, 69-77, 1 Dec. 2017 provides Cu/ZnO catalyst prepared by urea hydrolysis method. The catalyst was investigated for low-temperature methanol synthesis from syngas containing CO2. The activity of the conventional Cu/ZnO catalyst prepared by co-precipitation method was also compared.

U.S. Pat. No. 3,923,694A explains a methanol synthesis catalyst precursor comprising copper oxide and a support comprising spinel-forming metal oxides, spinel being present in crystallites not larger than 120 Angstrom units. This catalyst offers longer periods of methanol synthesis than a similar catalyst without spinel. A precipitation method for making the precursor is also described.

U.S. Pat. No. 7,820,128B2 relates to a process for preparing Cu/Zn/Al catalysts. In this process, the metals are used in the form of their formates and are precipitated in a suitable form. Suitable precipitants are, for example, alkali metal carbonates. The invention further relates to a catalyst as can be obtained by the process according to the invention and to its use.

The reported state of the art technology generally converts hydrocarbon feedstock into syngas and use thereof results into production of carbon dioxide which is a greenhouse gas and there is lot of environmental concerns regarding reducing the overall carbon footprints. Moreover, the prior art documents propose various valorization methods for hydrocarbon gasification to power, heat or fuel production.

Further, the usage of gasification products, preferably syngas directly for methanol production has been discussed in the above prior art documents. The main disadvantages of this method are selectivity to methanol in a syngas supplied reactor is less compared to the CO2 fed reactor thereby resulting in increased volume of by-products. Further, syngas to methanol reaction conditions is highly exothermic resulting in a demand for severe reaction conditions which makes the process energy intensive. Furthermore, in a syngas fed methanol reactor, freedom to adjust the reactant gas stoichiometric ratio is highly limited thereby restricting the possibility to operate the reactor at the optimized conditions.

Biomass waste management has been a huge problem since the amount of waste generated increases enormously every year. Besides biomass, coal and petcoke are high heating value feedstock which can be harnessed for power generation. Exploiting the energy potential of solid hydrocarbon feedstock has several ways out including combustion, gasification, incineration, pyrolysis, fermentation etc. However, a waste management option that is less polluting and offering conversion to a higher-grade produce along with voluminous size reduction is desirable.

Accordingly, there is a need of more energy efficient system and process which can reduce the overall carbon dioxide release into the environment and can also produce valuable byproducts.

SUMMARY OF THE INVENTION

The present disclosure provides an integrated process for generating electricity from a hydrocarbon feedstock and simultaneously synthesizing methanol through CO2 hydrogenation with the help of a Cu/Zn-based catalyst system. The process includes following steps:
(i) gasifying the hydrocarbon feedstock and oxygen inside a gasification unit to produce a syngas, wherein, the said syngas is used as a fuel for electrical power generation inside a power generation unit;
(ii) reusing a first part of an exhaust stream of the said power generation unit as a reactant in the said gasification unit, wherein, the first part of an exhaust stream comprises a fixed portion of $CO_2$ and water;
(iii) using a second part of the said exhaust stream as a reactant for methanol generation in a methanol reactor, wherein, the second part of the exhaust stream is cooled to separate $CO_2$ and water, and no CO2 capture system is required additionally, and $CO_2$ is used as the reactant for methanol synthesis;
(iv) operating an electrolyzer to produce hydrogen, wherein, a required stoichiometric ratio of the produced hydrogen is transferred into the methanol reactor for methanol synthesis, wherein, a Cu/Zn-based catalyst system is used inside the methanol reactor for methanol synthesis through direct hydrogenation of $CO_2$; and
(v) recovering and reusing an oxygen by-product from the said electrolyzer, wherein, the oxygen by-product is used as a gasifying agent in the said gasification unit and a combustion agent in the said power generation unit.

Wherein, the said electrolyzer is operated during non-peak hours by using a part of electrical power from the said power generation unit. The hydrocarbon feedstock is selected from biomass, coal or petcoke etc. The $CO_2$ of the first part of the said exhaust stream is converted into CO inside the said gasification unit, and $H_2O$ works as a gasifying agent inside the said gasification unit.

The Cu/Zn-based catalyst system is a heterogeneous catalyst of copper, zinc, Alumina, cerium, zirconium and gallium, and the said Cu/Zn-based catalyst system results hydrogenation of $CO_2$ at low temperature and high pressure. Further, the Cu/Zn based catalyst system provides a per-pass conversion of $CO_2$ equal to or higher than 65.56% and methanol yield more than 12.37% operating the methanol reactor under a specific reaction condition. Wherein, the specific reaction conditions of the methanol reactor have temperature in range of 200° C. to 320° C., pressure in range of 10 to 200 bar, $CO_2:H_2$ molar ratio in range of 1:2 to 1:10, and GHSV in range of 2000 to 10000 per hour. Specifically, the specific reaction conditions of the methanol reactor have temperature in range of 220° C. to 280° C., pressure in range of 40 to 60 bar, $CO_2:H_2$ molar ratio in range of 1:3 to 1:5, and GHSV in range of 4000 to 6000 per hour.

Accordingly, the process and system as disclosed herein aims at reducing the $CO_2$ footprints by utilizing syngas product of gasification for producing electricity and then utilizing the $CO_2$ exhaust of the power generation unit for methanol generation. This process reduces the $CO_2$ emission by converting the combusted exhaust product to intermediate chemicals or fuels thereby keeping carbon in the loop rather than discarding it to the atmosphere. The process also uses oxygen as the oxidizing agent in both gasification unit and power generation unit thereby circumventing the gas cleaning step post combustion. The produced syngas from gasification process can be passed through a power generation unit which gives pure $CO_2$ and $H_2O$ in the exhaust gas.

Further, a portion of the exhaust gas which is primarily a mixture of $CO_2$ and $H_2O$ is recycled back to the gasification unit, wherein, the $CO_2$ gets further converted into CO (according to the Boudouard gasification reaction) and $H_2O$ acts as a gasifying agent alongside oxygen. The $CO_2$ from the resultant stream is directly utilized for methanol generation after removal of moisture. The electricity from the power generation unit can be sent to the electrolyzer during off-peak hours for producing hydrogen and oxygen gases. The oxygen by-product of the electrolysis step is integrated as a gasifying agent in the gasification process and combusting agent in the power generation unit. This integration can be highly economic as it avoids the usage of a dedicated oxygen generation step to produce pure $O_2$ stream. Therefore, the above process and system can be considered as an integrated process that combines waste management, power generation, reduction of $CO_2$ footprints, fuel generation and $CO_2$ utilization.

Technical Advantages of the Invention

The present integrated process has the following advantage over the prior arts:

One advantage of the present integrated process is to convert solid hydrocarbon feedstock like waste biomass, coal and petcoke into methanol which is higher-value and cleaner-grade fuel product, and which is used in power generation.

Another advantage of the present integrated process is that there is no requirement of separate air separation unit to produce clean oxygen which is used as an oxidizing agent in the gasification and combustion units because the pure oxygen by-product stream obtained from the electrolysis unit perform this function.

Yet another advantage of present integrated process is that the usage of oxygen instead of air as a gasifying agent rules out the formation of impurities in the product gas mixture thereby producing a product mixture simply containing CO, $CO_2$, $H_2$ and $CH_4$.

Another advantage of present integrated process is that the use of oxygen in the syngas combustion within power generation unit excludes the need of $CO_2$ separation unit thereby providing simpler process set-up to obtain pure $CO_2$ stream.

Yet another advantage of the present integrated process is that the $CO_2$ and $H_2O$ from the exhaust gases of the power generation unit is recycled and reutilized in the gasification unit for further conversion to CO and $H_2$. The greenhouse gas $CO_2$ is utilized to produce cleaner fuel/chemical methanol rather than discarding as exhaust gas.

Another advantage of the present invention is that the $CO_2$ and $H_2$ streams thus obtained from power generation and electrolysis step respectively are pure streams thus enabling better hydrogenation yield to methanol.

Objectives of the Invention

The primary objective of the present integrated process is to provide value added methanol as well as electricity power from hydrocarbon feedstock gasification and reutilization of the carbon dioxide.

Further objective of the present integrated process is to minimize the carbon footprints of hydrocarbon feedstock treatment.

Further objective of the present integrated process is the biomass treatment to produce cleaner fuels and thus resulting in an overall reduction of environment pollution problem.

BRIEF DESCRIPTION OF THE DRAWING

To further clarify advantages and aspects of the present integrated process, a more particular description of the present integrated process will be rendered by reference to specific embodiments thereof, which is illustrated in the appended drawing(s). It is appreciated that the drawing(s) of the present integrated process depicts only typical embodiments of the invention and are therefore not to be considered limiting of its scope.

BRIEF DESCRIPTION OF THE INVENTION

Figure 1:
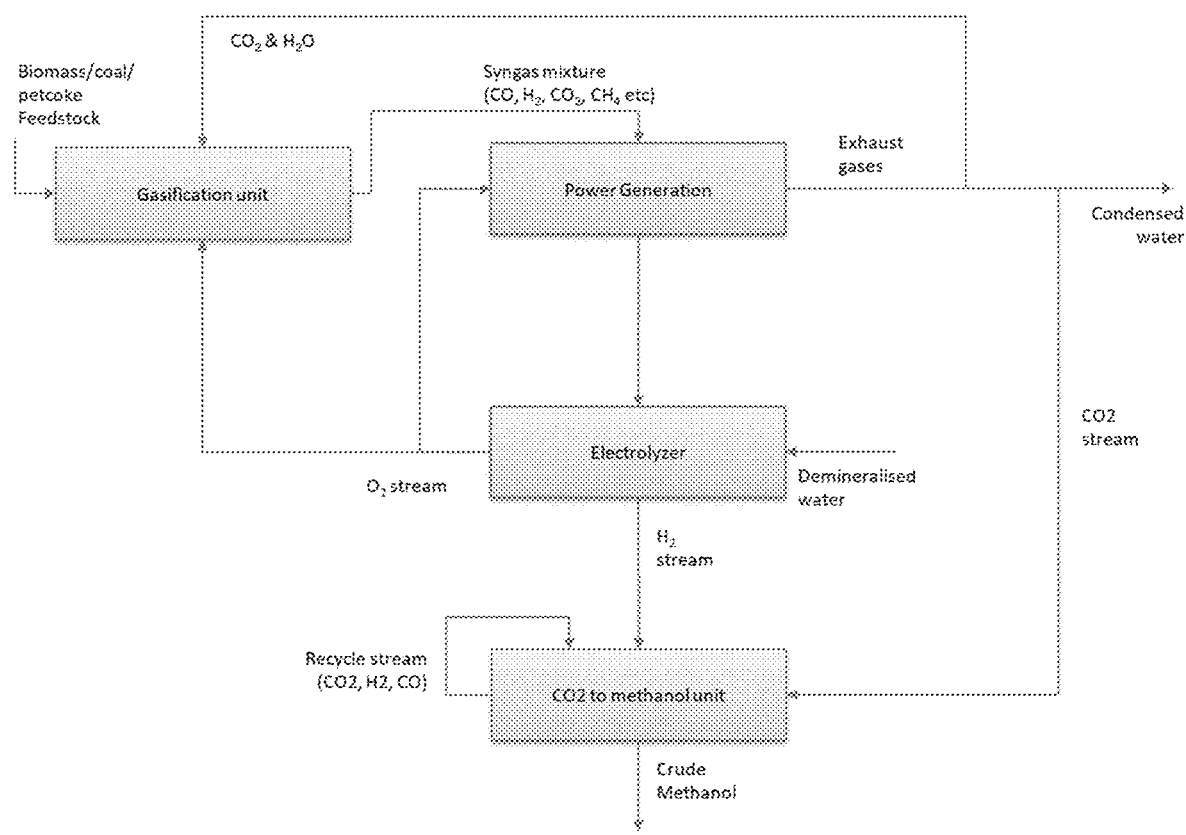
FIG. 1: illustrates a schematic process flow diagram depicting an integrated process scheme for the generation of electricity through gasification of the hydrocarbon feedstock along with conversion of CO2 to methanol.

Solid hydrocarbon feedstocks like coal, petcoke and biomass waste have a huge energy potential. For instance, biomass waste is a major source of renewable energy that is leaving the value chain untapped. The unbalanced waste management practice creates many threatening problems such as (i) huge land area occupied by landfill sites, (ii) Groundwater depletion due to accumulated wastes, (iii) greenhouse gas emissions from numerous waste filling sites, (iv) Marine life threats and many others. On the other side, the huge energy potential of biomass wastes provides an immediate solution to address this waste management problem by bringing the valuable energy from these wastes back to the cycle, i.e., practicing the so called 'circular economy'.

For years, solid wastes are mainly recycled, piled up in landfill sites or incinerated but all these conventional methods further create air pollution and greenhouse gas emission problem. However, thermal treatment of the waste material gives better control in energy recovery besides the huge volume reduction of the solid wastes. Incineration, pyrolysis, and gasification comprises the well-established thermal treatment methods. Incineration though harnesses certain segment of the energy potential also creates emission threats. Thus, pyrolysis and gasification are commercially way forward in waste to energy treatment with controlled emissions. However, in gasification almost 72% of the energy can be recovered with an investment of only 28% energy and the control of gasification process is much simpler compared to that of pyrolysis. Therefore, developing advanced 'waste to energy' gasification technology with integrated carbon looping is vital in achieving low-carbon targets especially, in hydrocarbon feedstock management and biomass waste management. The oxygen-based gasification process to produce methanol through heat, power and hydrocarbon feedstock integration provides a better solution for the above cited issues.

According to the main embodiment, the present disclosure provides an integrated process and system for utilizing hydrocarbon feedstock in methanol synthesis through CO2 conversion as well as electricity generation.

The integrated approach of the present disclosure suggests a superior alternative to use the waste biomass, coal or petcoke for electricity generation and also utilizing CO2 produced in process to methanol production. The present process utilizes multiple feedstocks for gasification using oxygen as a gasifying agent instead of air and the resultant product syngas is used as a fuel for power production. A portion of the exhaust gas from the power generation unit, containing CO2 and H2O streams is recycled back to the gasification unit for conversion to CO. The remaining gas is cooled for the removal of water and the resultant CO2 stream is sent to the methanol generation unit. The electricity produced is further used in an electrolyzer, especially, during non-peak hours for the production of H2 (with O2 as by-product) which is sent to the methanol reactor. The current approach provides a superior way for CO2 utilization to methanol as compared to the syngas-to-methanol pathway. Further, the integration of oxygen produced from the electrolyzer, as a by-product in the electrolyzer unit with both the gasification and power generation units where it is used as a gasifying agent and combustion agent respectively, reduces the capital cost as there is no need for an exclusive air separation unit. Further, this integration makes use of the by-product oxygen from electrolyzer unit as a reactant which otherwise would have been discarded.

The FIG. 1 explains the current invention of an advanced waste to energy conversion through carbon looping. The biomass feedstock basically includes agricultural residues, organic fractions of municipal solid wastes, paper, cardboard, plastic, food waste, green waste etc. The hydrocarbon feedstock to the gasification unit in the current scheme can be coal, petcoke or waste biomass. The solid hydrocarbon feedstock after suitable size reduction is fed to the gasification unit. The gasifying agent can be air, oxygen or steam. However, the oxygen and steam have considerable advantages over air as the gasifying agent. In the proposed present process and system, the oxygen is chosen as the preferred gasifying agent. In the present process the gasification products include a syngas mixture mainly consisting of CO, H2, CO2, CH4 etc. This product syngas mixture is used as a fuel for power generation. The combustion process in the power generation unit is supplied with oxygen (produced in the electrolyzer unit) as the combustion agent. A portion of the exhaust gases from the power generation unit, containing CO2 and H2O as primary constituents is recycled back to the gasification unit for further conversion into CO and H2. Wherein, the CO2 gets converted to CO inside the gasification chamber as per the Boudouard reaction. The H2O in the recycle gas acts as a gasifying agent along with O2 thereby promoting the formation of H2 of higher heating value. The remaining portion of the exhaust gas is cooled for removing the water content thereby producing a resultant pure CO2 stream. The CO2 stream thus produced is sent to the methanol generation system for further hydrogenation.

In an embodiment, during the peak hours, the electricity generated through this integrated gasification unit is sent to the main grid, attending the energy consumption of residential homes and industries. The electricity from the power generation unit can be sent to the electrolyzer during off-peak hours for generation of hydrogen. In the electrolyzer, demineralised water is split into H2 and O2 stream using the generated electricity from the power generation unit. The O2 stream from the electrolyzer is used in both the gasification and combustion units as mentioned above. This integration process as disclosed herein serves the purpose of cost reduction (of an exclusive air separation unit for O2 production), by-products recycling (using the by-product O2 stream from electrolyzer as the high-quality oxidizing agent) and exclusion of a separate CO2 capture system. Further, the H2 stream from the electrolyzer is sent to the methanol reactor in the required stoichiometric proportion for production of methanol.

Figure 2:
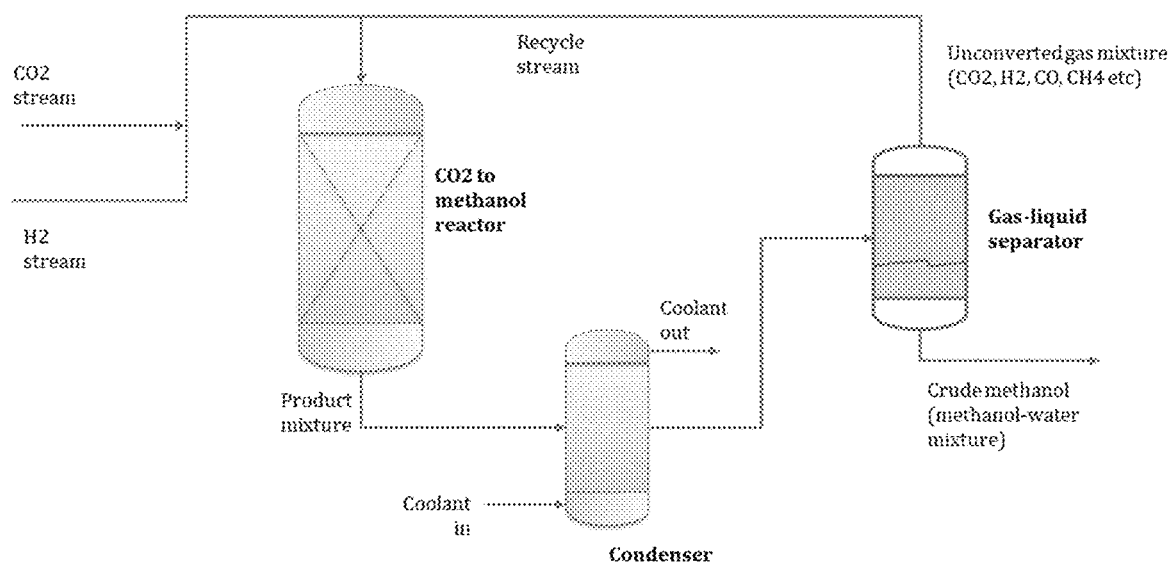
FIG. 2: illustrates a schematic process flow diagram depicting CO2 to methanol conversion process setup.
Figure 3A:
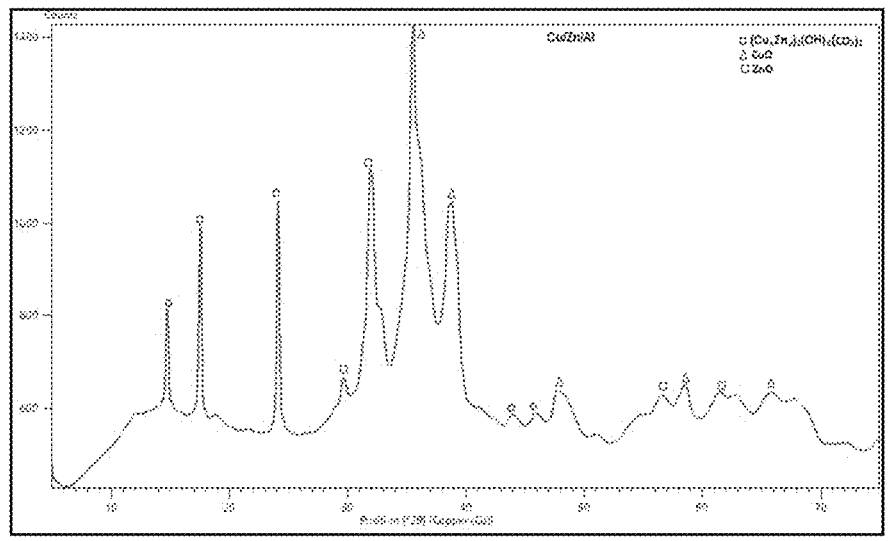
FIG. 3(a): illustrates an XRD chromatogram of Cu/Zn/Al catalyst.
Figure 3B:
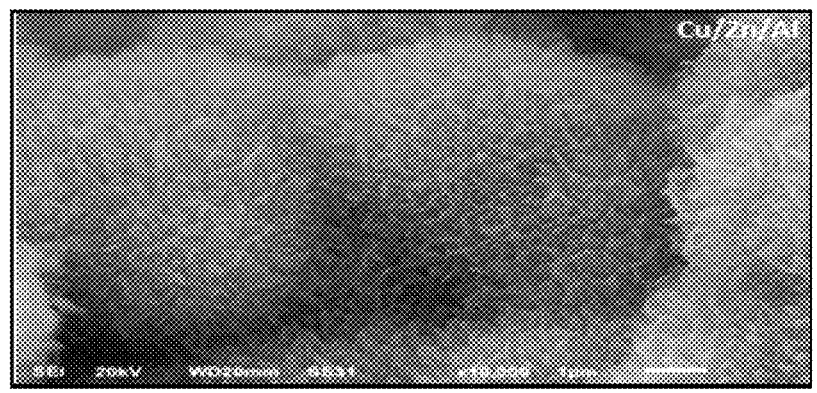
FIG. 3(b): illustrates a surface morphology (SEM image) of Cu/Zn/Al catalyst.
Figure 4A:
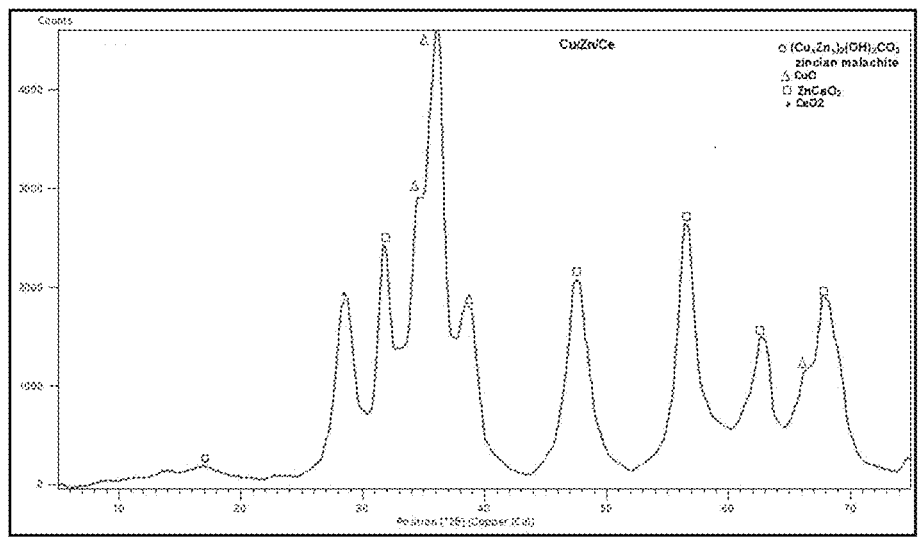
FIG. 4(a): illustrates an XRD chromatogram of Cu/Zn/Ce catalyst.
Figure 4B:
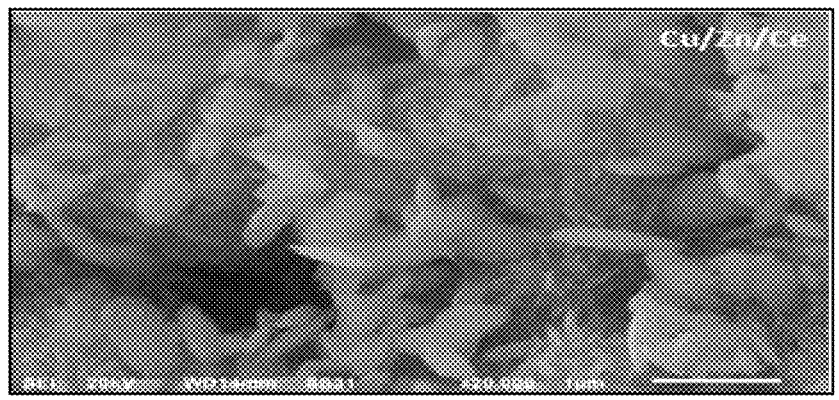
FIG. 4(b): illustrates a surface morphology (SEM image) of Cu/Zn/Ce catalyst.
Figure 5A:
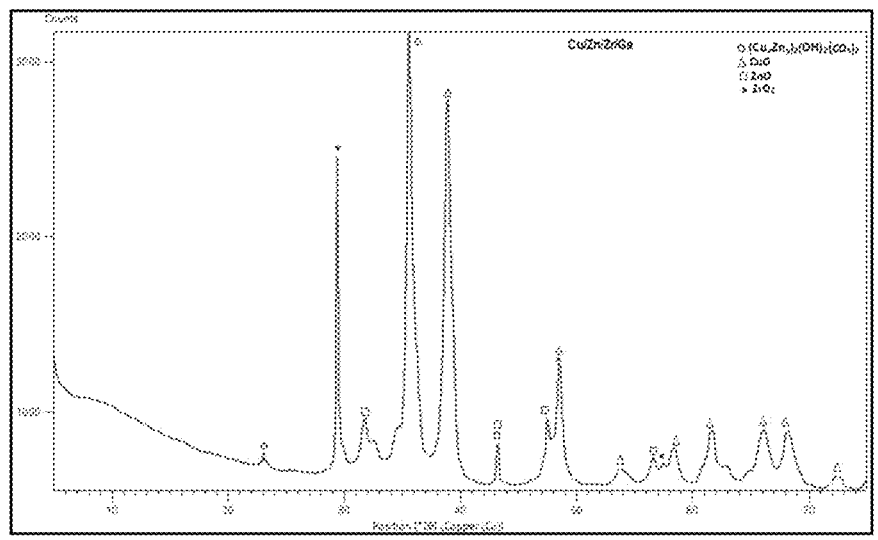
FIG. 5(a): illustrates an XRD chromatogram of Cu/Zn/Zr/Ga catalyst.
Figure 5B:
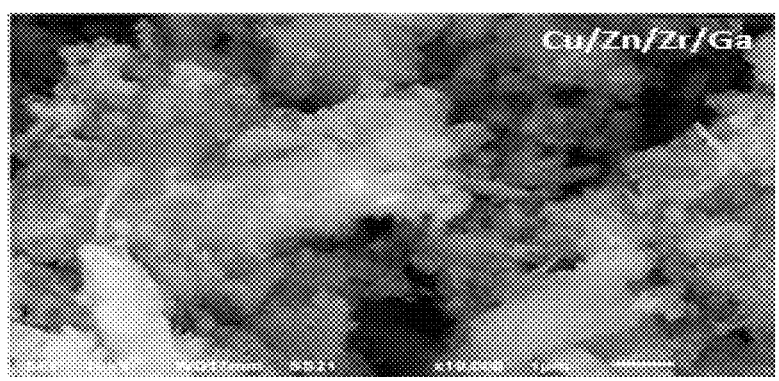
FIG. 5(b): illustrates a surface morphology (SEM image) of Cu/Zn/Zr/Ga catalyst.

The FIG. 2 depicts a CO2 to methanol system setup which includes a feed section, a reactor section and product separation section. The feed section includes CO2, H2 and N2 streams. The CO2 line includes a booster and heat traced line. All the gas feeds are fitted with pressure regulators, hand valves and mass flow controllers for ensuring the required feed ratio of CO2:H2 to the inlet of the reactor. The N2 gas stream is used for diluting the hydrogen stream during catalyst activation. All the gas streams to the reactor inlet are sufficiently pure (99.9 to 99.999%). The reactor is adapted to convert CO2 to methanol and selected from a fixed-bed reactor, a down-flow reactor and/or a single pass configuration. The flow rates of the individual gas streams are controlled by mass flow controllers. CO2 and H2 in the required composition are premixed before the reactor inlet. The reactor is heated through electrical furnace and the surface of the reactor is insulated to avoid heat loss. The product stream from the reactor outlet passes to the condenser followed by gas-liquid separator. The condenser has a cooling range of (0° C. to 20° C.) and liquefies the water and methanol product from the unconverted gas stream. In the gas-liquid separator, the product liquid stream gets segregated from the gas effluent stream at a pressure of 10 to 20 bar. The liquid product stream is then depressurized through a pressure control valve and passed on to the product vessel for further analysis. The gas stream passes through a wet gas flow meter for the flow measurement and analyzed for individual gas compositions and recycled back to the reactor for converting CO2 to methanol, wherein, a Cu/Zn-based catalyst provides conversion of CO2 to methanol.

There are very limited studies on Cu/Zn-based catalyst and their preparation process, and the present disclosure specifically provides preparation process of Cu/Zn-based catalyst by using carbamide as an ideal chemical solution. The current process aims at the facile and accelerated precipitation reaction of the Cu/Zn-based catalyst in autoclave reactor under high temperature autogenic pressure conditions. Different heterogeneous catalyst systems of copper, zinc, Alumina, cerium, zirconium and gallium are used for catalysts synthesis with improved properties like better metal ions dispersion, high surface area and high thermal stability.

Accordingly, the present disclosure provides a Cu/Zn-based catalyst for methanol synthesis through direct hydrogenation reaction of CO2. The said Cu/Zn-based catalyst comprises a nitrate or an acetate salt of copper, zinc, and one or more nitrate salts of metals selected from alumina, cerium, zirconium, gallium.

Further, the Cu/Zn-based catalyst as disclosed herein includes a nitrate or an acetate salt of copper, zinc, and a nitrate salt of alumina, forming a copper/zinc/alumina catalyst, wherein, copper, zinc, alumina each are in weight % ratio of 6.5:2.5:1.

Further, the Cu/Zn-based catalyst as discussed herein includes a nitrate or an acetate salt of copper, zinc, and a nitrate salt of cerium, forming a copper/zinc/cerium catalyst, wherein, copper, zinc, cerium each are in weight % ratio of 2.7:3.5:1.

Further, the Cu/Zn-based catalyst as disclosed herein includes a nitrate or an acetate salt of copper, zinc, and a nitrate salt of zirconium, and/or gallium, forming a copper/zinc/zirconium/gallium catalyst, wherein, copper, zinc, zirconium, gallium each are in weight % ratio of 5.5:3:1:0.5.

Further, the Cu/Zn-based catalyst as disclosed herein shows 10.42 to 19.97 weight % loss at a reaction temperature of 900° C. and surface area is 87 to 103 m2/gm.

Furthermore, the present disclosure provides a process for preparing the Cu/Zn-based catalyst, wherein, the process comprises a precipitation reaction of a reaction mixture of a nitrate salt, or an acetate salt of metals selected from copper, zinc, and one or more nitrate salt of metals selected from alumina, cerium, zirconium, gallium. Wherein, the said precipitation reaction is carried out in an autoclave reactor under 100° C. to 140° C. temperature condition and 25 bar autogenic pressure condition.

The precipitation reaction of the said reaction mixture is initiated by adding an aqueous solution of carbamide which acts as mild precipitating agent and lifts the pH of the reaction mixture to 13.9.

Methanol Production, Catalyst, and Operating Parameters:

The different catalysts are experimented for methanol production by varying operating parameters like temperature, pressure, CO2:H2 ratio and GHSV. The temperature range can vary from 200° C. to 320° C. more specifically between 220° C. to 280° C. The pressure can vary from 10 to 200 bar more specifically from 40 to 60 bar; the methanol formation is favored at higher pressures according to Le-Chatelier's principle. The CO2:H2 ratio can vary from 1:2 to 1:10, more specifically from 1:3 to 1:5. The GHSV which is the gas hourly space velocity is varied from 2000 to 10000 $hr^{-1}$, more specifically in the range from 4000 to 6000 $hr^{-1}$.

Example-1

Cu/Zn/Al Catalyst Synthesis:

The catalyst precursor powder Cu/Zn/Al was prepared with the high pressure solvothermal hydrolysis method. The matrix of the catalyst composition (wt. %) is 6.5:2.5:1. The catalyst is synthesized through the following steps, 1. The autoclave reactor is charged with an aqueous solution containing $Cu(CH_3CO_2)_2 \cdot 2H_2O$ (3.72 M), $Zn(CH_3CO_2)_2 \cdot 2H_2O$ (1.40M) and $Al(NO_3)_3 \cdot 9H_2O$ (1.31M) mixed in an molar ratio of 0.11:0.04:0.04. The pH of the resultant reaction mixture is 6.5.
2. An aqueous solution of carbamide (0.26 mole content) is added as a mild precipitating agent which lifts the pH value of the mixture to 13.9.
3. The autoclave is tightly closed and run for set 100° C.-140° C. temperature for 4 hours under autogenic pressure (25 bar). During the reaction, metal ions are precipitated by the hydroxide ions that are formed by precipitant.
4. The precipitated product was aged overnight, filtered and washed with distilled water until neutral (pH 7) reaction medium is obtained.
5. The obtained precipitates were dried in an oven at 100° C.-140° C. for 4 hours and then calcined at 220° C. for 4 to 5 hrs.
6. Final Cu/Zn/Al catalyst is obtained as course black powder and is characterized by XRD (phase analysis), ICAP (metal content analysis), SEM (morphology analysis), TGA (thermal stability) and Surface area (morphology analysis).

Cu/Zn/Al Catalyst Testing:

The Cu/Zn/Al catalyst as disclosed herein is tested under various temperatures, pressures, GHSVs and CO2:H2 ratios as per the procedure described under detailed description of FIG. 1 and FIG. 2. The highest CO2 conversion and methanol selectivity obtained for this catalyst was shown to be 65.56% and 21.49%. The table-1a below enlists the CO2 conversion, methanol selectivity and methanol yield obtained for this catalyst at varying operating conditions.

TABLE-1a

| Catalyst composition: X % Cu/y % Zn/z % Al | CO2 conversion, % | Methanol selectivity, % | Methanol Yield, % |
|---|---|---|---|
| T = 260° C., P = 60 bar, GHSV = 5250 hr-1, CO2:H2 = 1:3 | 57.74 | 15.27 | 8.82 |
| T = 260° C., P = 40 bar, GHSV = 5250 hr-1, CO2:H2 = 1:3 | 28.14 | 19.79 | 5.57 |
| T = 260° C., P = 50 bar, GHSV = 5250 hr-1, CO2:H2 = 1:3 | 30.71 | 20.48 | 6.29 |
| T = 260° C., P = 70 bar, GHSV = 5250 hr-1, CO2:H2 = 1:3 | 40.52 | 21.49 | 8.71 |
| T = 240° C., P = 70 bar, GHSV = 5250 hr-1, CO2:H2 = 1:3 | 65.56 | 12.46 | 8.17 |

Cu/Zn/Al Catalyst Physico-Chemical Properties:

Various physico-chemical properties of the Cu/Zn/Al catalyst are determined through the standard and general test methods such as Inductively coupled plasma (ICP-AES), Thermo gravimetric analysis (TGA), Surface Area (SA), XRD (X-ray diffraction), Scanning electron microscope (SEM) analysis. Test results are presented in the below table-1b.

TABLE-1b

| S. No. | Property | Cu/Zn/Al |
|---|---|---|
| 1. | ICAP (%) | Cu-41.32 Zn-15.60 Al-8.37 |
| 2. | TGA (wt. loss, wt. %) (RT-900° C.) | 11.04 |
| 3. | Surface Area (m$^2$/gm) | 103 |

Example-2

Cu/Zn/Ce Catalyst Synthesis:

The catalyst precursor powder Cu/Zn/Ce was prepared with the high pressure solvothermal hydrolysis method. The matrix of the catalyst composition (wt. %) is 2.7:3.5:1. The catalyst is synthesized through the following steps, 1. The autoclave reactor is charged with an aqueous solution containing $Cu(CH_3CO_2)_2 \cdot 2H_2O$ (2.64M), $Zn(CH_3CO_2)_2 \cdot 2H_2O$ (3.42M), $Ce(NO_3)_2 \cdot 6H_2O$ (0.44M) mixed in an molar ratio of 0.079:0.101:0.013. The pH of the resultant reaction mixture is 6.5.
2. An aqueous solution of carbamide (0.26 mole content) is added as mild precipitating agent which lifts the pH of the mixture to 13.9.
3. The autoclave is tightly closed and run for set 100° C.-140° C. temperature for 4 hours under autogenic pressure (25 bar). During the reaction, metal ions are precipitated by the hydroxide ions that are formed by precipitant.
4. The precipitated product was aged overnight, filtered and washed with distilled water until a neutral (pH 7) reaction medium is obtained.
5. Obtained precipitates were dried in an oven at 100° C.-140° C. for 4 hours and then calcined at 220° C. for 4 to 5 hrs.
6. Final Cu/Zn/Ce catalyst is course black powder, characterized by XRD (phase analysis), ICAP (metal content analysis), SEM (morphology analysis), TGA (thermal stability) and Surface area (morphology analysis).

Cu/Zn/Ce Catalyst Testing:

The Cu/Zn/Ce catalyst of the present invention is tested under various temperatures, pressures, GHSVs and CO2:H2 ratios as per the procedure described under detailed description of FIG. 1 and FIG. 2. The highest CO2 conversion and methanol selectivity obtained for this catalyst was shown to be 50.86% and 60.18%. The table-2a enlists the CO2 conversion, methanol selectivity and methanol yield obtained for this catalyst at varying operating conditions.

TABLE-2a

| Catalyst composition: X % Cu/y % Zn/z % Ce | CO2 conversion, % | Methanol selectivity, % | Methanol Yield, % |
|---|---|---|---|
| T = 320° C., P = 65 bar, GHSV = 5242 hr-1, CO2:H2 = 1:3 | 20.55 | 60.18 | 12.37 |
| T = 320° C., P = 60 bar, GHSV = 5242 hr-1, CO2:H2 = 1:5 | 23.82 | 42.74 | 10.18 |
| T = 320° C., P = 60 bar, GHSV = 4250 hr-1, CO2:H2 = 1:3 | 15.41 | 59.44 | 9.16 |
| T = 320° C., P = 60 bar, GHSV = 7250 hr-1, CO2:H2 = 1:3 | 50.86 | 12.47 | 6.34 |
| T = 280° C., P = 60 bar, GHSV = 5242 hr-1, CO2:H2 = 1:3 | 20.9 | 29.23 | 6.11 |

Cu/Zn/Ce Catalyst Physico-Chemical Properties:

Various physico-chemical properties of the Cu/Zn/Ce catalyst are determined through the standard and general test methods such as Inductively coupled plasma (ICP-AES), Thermo gravimetric analysis (TGA), Surface Area (SA), XRD (X-ray diffraction), Scanning electron microscope (SEM) analysis. Test results are presented in the below table-2b.

TABLE-2b

| S. No. | Property | Cu/Zn/Ce |
|---|---|---|
| 1. | ICAP (%) | Cu-27.3 |
|  |  | Zn-37.4 |
|  |  | Ce-8.42 |
| 2. | TGA (wt. loss, wt. %) (RT-900° C.) | 10.42 |
| 3. | Surface Area (m$^2$/gm) | 87 |

Example-3

Cu/Zn/Zr/Ga Catalyst Synthesis:

The catalyst precursor powder Cu/Zn/Zr/Ga was prepared with the high pressure solvothermal hydrolysis method. The matrix of the catalyst composition (wt. %) is 5.5:3:1:0.5. The catalyst is synthesized through the following steps, 1. The autoclave reactor is charged with an aqueous solution of metal salts containing Cu(NO3)2.3H2O (1M), Zn(NO3)2.6H2O (1M), ZrO(NO3)2.H2O and Ga(NO3)2.3H2O (1M) mixed in an molar ratio of 0.34:0.18:0.043:0.028. The pH of the resultant reaction mixture is 6.5.
2. An aqueous solution of carbamide (0.26 mole content) as mild precipitating agent was added, lifting pH of the mixture to 13.9.
3. The autoclave is tightly closed and run for set 100° C.-140° C. temperature for 4 hours under autogenic pressure (25 bar). During the reaction, metal ions are precipitated by the hydroxide ions that are formed by precipitant.
4. The precipitated product was aged overnight, filtered and washed with distilled water up to neutral (pH 7) reaction medium.
5. Obtained precipitates were dried in oven at 100° C.-140° C. for 4 hours and then calcined at 220° C. for 4-5 hrs.
6. Final Cu/Zn/Zr/Ga catalyst is a course black powder and is characterized by XRD (phase analysis), ICAP (metal content analysis), SEM (morphology analysis), TGA (thermal stability) and Surface area (morphology analysis).

(Cu/Zn/Zr/Ga Testing)

The Cu/Zn/Zr/Ga catalyst of the present invention is tested under various temperatures, pressures, GHSVs and CO2:H2 ratios as per the procedure described under detailed description of FIG. 1 and FIG. 2. The highest CO2 conversion and methanol selectivity obtained for this catalyst was shown to be 25.74% and 41.45%. The table-3a enlists the CO2 conversion, methanol selectivity and methanol yield obtained for this catalyst at varying operating conditions.

TABLE-3a

| Catalyst composition: X % Cu/y % Zn/z % Zr/c % Ga | CO2 conversion, % | Methanol selectivity, % | Methanol Yield, % |
|---|---|---|---|
| T = 340° C., P = 60 bar, GHSV = 8000 hr-1, CO2:H2 = 1:3 | 23.42 | 38.47 | 9.01 |
| T = 300° C., P = 60 bar, GHSV = 8000 hr-1, CO2:H2 = 1:3 | 21 | 41.45 | 8.7 |
| T = 380° C., P = 60 bar, GHSV = 8000 hr-1, CO2:H2 = 1:3 | 25.74 | 32.23 | 8.29 |
| T = 260° C., P = 60 bar, GHSV = 8000 hr-1, CO2:H2 = 1:3 | 16.82 | 36.7 | 6.17 |
| T = 340° C., P = 60 bar, GHSV = 5000 hr-1, CO2:H2 = 1:3 | 15.64 | 37.36 | 5.84 |

Cu/Zn/Zr/Ga Catalyst Physico-Chemical Properties:

Various physico-chemical properties of the Cu/Zn/Zr/Ga catalyst are determined through the standard and general test methods such as Inductively coupled plasma (ICP-AES), Thermo gravimetric analysis (TGA), Surface Area (SA), XRD (X-ray diffraction), Scanning electron microscope (SEM) analysis. Test results are presented in the below table-3b.

TABLE-3b

| S. No. | Property | Cu/Zn/Zr/Ga |
|---|---|---|
| 1. | ICAP (%) | Cu-40.7 |
|  |  | Zn-8.5 |
|  |  | Zr-4.2 |
|  |  | Ga-2.04 |
| 2. | TGA (wt. loss, wt. %) (RT-900° C.) | 19.97 |
| 3. | Surface Area (m$^2$/gm) | 90 |

Catalyst Physical Property Characterization Methods

Inductively coupled plasma (ICP-AES) and Thermo gravimetric analysis (TGA) were performed by standard test methods while the Surface Area (SA), XRD (X-ray diffraction), Scanning electron microscope (SEM) analysis were performed by general procedure. For validation, instrument model numbers as used hereinafter are for reference only.

Inductively Coupled Plasma (ICP-AES)

Inductively coupled plasma (ICP) optical emission spectroscopy was used for the determination of metal content of the catalyst. The measurements were performed with a Perkin Elmer Optima 8300 DV spectrometer using ASTM D8088-16.

Thermo Gravimetric Analysis (TGA)

This test method is an empirical technique in which the mass of a substance, heated from room temperature to 900° C. at a heating rate of 10° C. min-1 under N2 atmosphere. TGA profile of the catalyst was recorded by TG model 2950 Hi Resolution modulated TGA by ASTM E1131-20 test methods.

Surface Area

The surface area of prepared catalyst was measured by Micromeritics BELSORB-Max PC000668 instrument through adsorption desorption measurements. The sample was degassed under vacuum at 400° C. for 2 hours prior to adsorption measurements to evacuate the physisorbed moisture.

XRD (X-Ray Diffraction)

The X-ray diffraction (XRD) patterns of catalysts were recorded on PAN Analytical Empyrean X-ray diffractometer (XRD) with Cu—K radiation at 45 kV and 40 mA. The catalyst powder was grinded fine to ensure random orientation of the molecules so that there are sufficient number of crystals to generate detectable signals of all angles respective to all the components present in the catalyst. The overall peak intensities are often used to estimate the amount of specific crystalline phases.

Scanning Electron Microscope (SEM)

SEM analysis was used to study the surface morphologies of catalysts. The topographical images of the catalyst sample were captured by type JSM-6610LV, JEOL, Japan coupled with X-ray energy dispersive spectroscopy. The morphology was observed using an energy dispersive X-ray system.

The above disclosed Cu/Zn-based catalysts and their use in the present process and system provides various technical advantages as outlined hereinafter. The catalyst synthesis process involves gradual in-situ dissolution of carbamide under pressure. With the increase of process temperature to 120° C., the degree and rate of precipitating agent increases and results in high surface area and well dispersed small sized Cu/Zn particles. Further, carbamide acts as mild precipitating agent with gradual dissolution effectively controls the nucleation rate of the reaction and results in uniform multi-component dispersion. The prepared catalyst has improved catalytic activity. The use of non-toxic, harmless carbamide compounds as precipitating agent merits to environmentally friendly catalyst for methanol synthesis. Further, the catalyst preparation process does not produce wastewater to the environment unlike the other conventional basic precipitants (NaOH, Na2CO3) and the precipitant aqueous solution can be stored, dosed and decomposed quite easily. Effluent recovered after catalyst washing can be served as N-based fertilizer.

The catalyst synthesized through the above novel method gives better single pass CO2 conversion and methanol yield of 65.56% and 12.37% respectively at the optimized process conditions including temperature, pressure, CO2:H2 ratio and GHSV.

Further, the catalyst synthesis process is simple, requires less quantity of metal loading and less reaction time. The catalyst synthesis process is cost effective due to use of inexpensive mild carbamide precipitant. Present in-situ hydrolysis of precipitating agent under pressure provides uniform metal ions dispersion and high surface area catalyst with enhanced catalytic activity.

Further, the carbamide precipitant does not require extra storage and special handling care. In general, prepared catalyst is thermally stable up to 800° C. in comparison to commercial catalysts. Introduction of carbamide as precipitant, increases the activity of the catalyst. The catalyst for methanol synthesis gives better CO2 conversion at the optimized process conditions.

Regarding the hydrocarbon gasification process provided by the present disclosure, it is noted that the oxygen supplied gasification units and combustion units require a dedicated air-separation unit (ASU) for the supply of pure oxygen. The cost of these ASUs account for almost 30% of capital cost since the separation of oxygen from atmospheric air is highly energy intensive. The suggested integration scheme provides a superior option for pure oxygen supply by integrating the electrolyzer unit with the gasification and combustion units thereby neglecting the usage of expensive ASU. Therefore, employing the pure oxygen gas which is a by-product of the electrolyzer unit, as an oxidizing agent in the gasification and combustion units addresses the higher capital investment of the otherwise non-integrated system.

Further, the oxygen is a superior gasifying agent as well as combustion agent not only because of the better gasification and combustion efficiencies, but also it produces a product gas mixture comprising fewer impurities. However, air supplied units produce a product mixture comprising 40 to 60% N2. This is a drawback because the air contains up to 79% nitrogen, leading to the produced gas being highly diluted (with low heating value 3.5-7.8 MJ/m3), which increases the cost of gas separation. Therefore, the usage of air as gasification/combustion agent is often limited to on-site heat and power generation.

Further, the increase in the oxygen proportion of air improves the oxidation of tar and char compounds, which diminishes the char and tar content while producing CO and CO2. Thus, the drawbacks of air gasification/combustion like low combustion efficiency, low heating value product gas, high proportion of impurities and deprived oxidation of tar and char compounds in the product gas mixture are addressed by the selection of pure oxygen.

Further, in the conventional process of hydrocarbon feedstock gasification, the air combusted unit in power generation produces a gas mixture which needs to be removed of N2 impurities followed by the separation/capture of CO2. This leads to additional cost to the overall system. However, the suggested integration scheme rules out the need for additional impurities separation cost. The CO2 separation from the combustion exhaust gas can be achieved through a simple cooling unit which primarily removes the water content from the exhaust stream.

Furthermore, in the present integrated process a portion of the exhaust stream from the power generation unit is recycled back to the gasification unit. The exhaust stream from the power generation unit predominantly contains CO2 and H2O. Recycling a portion of this stream, aids in the conversion of CO2 to CO according to the Boudouard gasification reaction. Therefore, the CO2 emissions from the combustion unit are utilized in the gasification unit for further production of valuable syngas. Also, the H2O composition in the exhaust gas will act as a superior gasifying agent in addition to oxygen, as steam gasification produces a greater amount of H2 with a higher heating value. This is attributed to steam's role in promoting the water-gas shift and steam reforming reactions. In addition, steam decreases the mass yield of tar and char in the final product mixture.

Accordingly, from the resultant stream of the combustion exhaust gases, pure CO2 stream is obtained post cooling without capture and the pure H2 stream is obtained from the electrolyser unit. The usage of these streams for direct hydrogenation to produce methanol is proven to be advantageous over the direct usage of syngas to produce methanol. CO2-to-methanol reaction is more selective towards methanol thereby resulting in fewer by-products, and the reaction conditions are milder because CO2 to methanol reaction is less exothermic compared to the syngas to methanol reaction. Further, the present integrated process also offers better carbon utilization compared with conventional syngas. Also, the freedom of adjusting the feed gas stoichiometric ratio depending on the catalyst requirements is superior in the present integrated process, wherein, CO2 and H2 are added as separate pure streams when compared to the syngas which is generated as a mixture of gases in the conventional processes.

The CO2 stream from the oxygen-combusted power generation unit is used for methanol generation rather than discarding as exhaust gas. Therefore, the otherwise polluting greenhouse gas is utilized to produce cleaner fuel/chemical-methanol through the catalytic hydrogenation process.

We claim:

1. An integrated process for synthesizing methanol from $CO_2$ and generating electricity from a hydrocarbon feedstock, wherein the process comprising the steps of:

(i) gasifying the hydrocarbon feedstock and oxygen inside a gasification unit to produce a syngas, wherein the syngas is used as a fuel for electrical power generation inside a power generation unit, wherein the power generation unit is configured to produce an exhaust stream, and wherein the exhaust stream comprises $CO_2$ and water;

(ii) reusing a first part of the exhaust stream of the power generation unit as a reactant in the gasification unit, wherein the first part of the exhaust stream comprises a fixed portion of $CO_2$ and water;

(iii) using a second part of the exhaust stream of the power generation unit as a reactant for methanol generation in a methanol reactor, wherein the second part of the exhaust stream is treated to separate $CO_2$ and water, and the separated $CO_2$ is used as the reactant for methanol synthesis;

(iv) operating an electrolyzer during non-peak hours to produce hydrogen and oxygen as a by-product, wherein a required stoichiometric ratio of the produced hydrogen is transferred into the methanol reactor for methanol synthesis, wherein a Cu/Zn-based catalyst system is used inside the methanol reactor for methanol synthesis through direct hydrogenation reaction of $CO_2$; and (v) recovering and reusing oxygen by-product from the electrolyzer, wherein the oxygen by-product is used as a gasifying agent in the gasification unit and a combustion agent in the power generation unit.

2. The integrated process as claimed in claim 1, wherein the Cu/Zn-based catalyst system is a heterogeneous catalyst of copper and zinc, and one or more metals selected from alumina, cerium, zirconium, and gallium.

3. The integrated process as claimed in claim 2, wherein the Cu/Zn-based catalyst system results hydrogenation of $CO_2$ and provides per-pass conversion of $CO_2$ equal to or higher than 65.56% and methanol yield more than 12.37%.

4. The integrated process as claimed in claim 3, wherein the methanol reactor has a temperature in a range of 200° C. to 320° C., a pressure in a range of 10 to 200 bar, a molar ratio of $CO_2:H_2$ in a range of 1:2 to 1:10, and a gas hourly space velocity (GHSV) in a range of 2000 to 10000 per hour.

5. The integrated process as claimed in claim 4, wherein the methanol reactor has the temperature in a range of 220° C. to 280° C., the pressure in a range of 40 to 60 bar, the molar ratio of $CO_2:H_2$ in a range of 1:3 to 1:5, and the GHSV in a range of 4000 to 6000 per hour.

6. The integrated process as claimed in claim 1, wherein the hydrocarbon feedstock is a biomass material, coal or petcoke.

7. The integrated process as claimed in claim 1, wherein the $CO_2$ of the first part of the exhaust stream is converted into CO inside the gasification unit, and $H_2O$ works as a gasifying agent inside the gasification unit.

8. The integrated process as claimed in claim 1, wherein the electrolyzer is operated by a portion of electrical power generated by the power generation unit.

9. The integrated process as claimed in claim 1, wherein the methanol reactor is selected from a fixed-bed reactor, a down-flow reactor and a single pass configuration reactor.

* * * * *